US00PP36356P2

(12) United States Plant Patent
Xiangang et al.

(10) Patent No.: US PP36,356 P2
(45) Date of Patent: Dec. 31, 2024

(54) ***HOYA* PLANT NAMED 'GREY FAIRY'**

(50) Latin Name: ***Hoya carnosa* x *serpens***
Varietal Denomination: Grey Fairy

(71) Applicant: Anhui Jadeite Garden Co., Ltd, Chuzhou (CN)

(72) Inventors: Shen Xiangang, Chuzhou (CN); Wang Dongliang, Chuzhou (CN); Wu Wanying, Chuzhou (CN)

(73) Assignee: Anhui Jadeite Garden Co., Ltd (CN)

( * ) Notice: Subject to any disclaimer, the term of this patent is extended or adjusted under 35 U.S.C. 154(b) by 0 days.

(21) Appl. No.: 18/372,203

(22) Filed: Sep. 25, 2023

(51) Int. Cl.
*A01H 5/02* (2018.01)
*A01H 6/08* (2018.01)

(52) U.S. Cl.
USPC ..... Plt./380
CPC ..... *A01H 6/08* (2018.05)

(58) Field of Classification Search
USPC ..... Plt./380
CPC ..... A01H 5/02
See application file for complete search history.

(56) References Cited

PUBLICATIONS https://www.facebook.com/jadeitegardenusstore/; Aug. 22, 2021; 5 pages.*

* cited by examiner

*Primary Examiner* — Kent L Bell

(57) ABSTRACT

A new and distinct *Hoya* plant named 'GREY FAIRY' is disclosed, characterized by stable silver-white foliage which does not fade. The new variety is a *Hoya*, typically produced as an indoor ornamental plant.

4 Drawing Sheets

Latin name of the genus and species: *Hoya carnosa* x *serpens*.

Variety denomination: 'Grey Fairy'.

BACKGROUND OF THE INVENTION

The new cultivar is a spontaneous mutation. The new variety was discovered as an uninduced branch mutation by the inventors on a plant of the parent variety, the unpatented *Hoya carnosa* x *serpens* 'Mathilde' in April 2021 at a nursery in Chuzhou, China.

Asexual reproduction of the new cultivar 'GREY FAIRY' was first performed in. Chuzhou, China by terminal vegetative cuttings in 2021. Subsequent asexual propagation has shown that the unique features of this cultivar are stable and reproduced true to type.

The following trait has been repeatedly observed and are determined to be the unique characteristic of 'GREY FAIRY'. This characteristic distinguishes 'GREY FAIRY' as a new and distinct *Hoya* cultivar:

1. Stable silver-white foliage which does not fade.

PARENT COMPARISON

Plants of the new cultivar 'GREY FAIRY' are similar to the parent in most horticultural characteristics. The new variety, however, differs in the following:

1. Foliage of the new variety is silver-white; foliage of the parent variety is green.

COMMERCIAL COMPARISON

'GREY FAIRY' can be compared to the commercial variety *Hoya* 'Eskimo', unpatented. Plants of 'Eskimo' are similar to plants of 'GREY FAIRY' in most horticultural characteristics, however, plants of 'GREY FAIRY' differ in the following:

1. Foliage color of 'Grey Fairy' is silver-white; foliage color of this comparator is green with silver flecks.
2. Leaf shape of 'Grey Fairy ' is orbicular; foliage shape of 'Eskimo' is deltate.

BRIEF DESCRIPTION OF THE PHOTOGRAPHS

The accompanying drawing in FIG. 1 illustrates in full color a typical plant of 'GREY FAIRY'.

Figure 1:
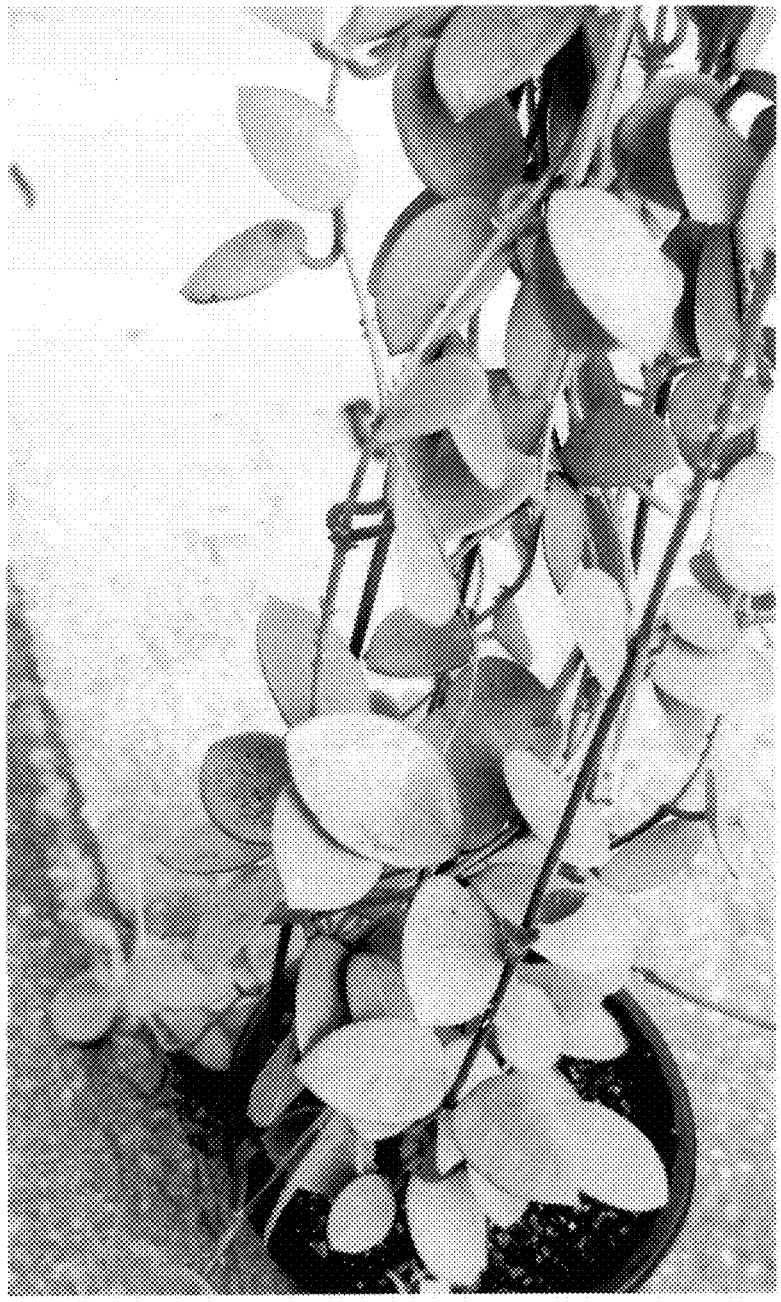
Figure 2:
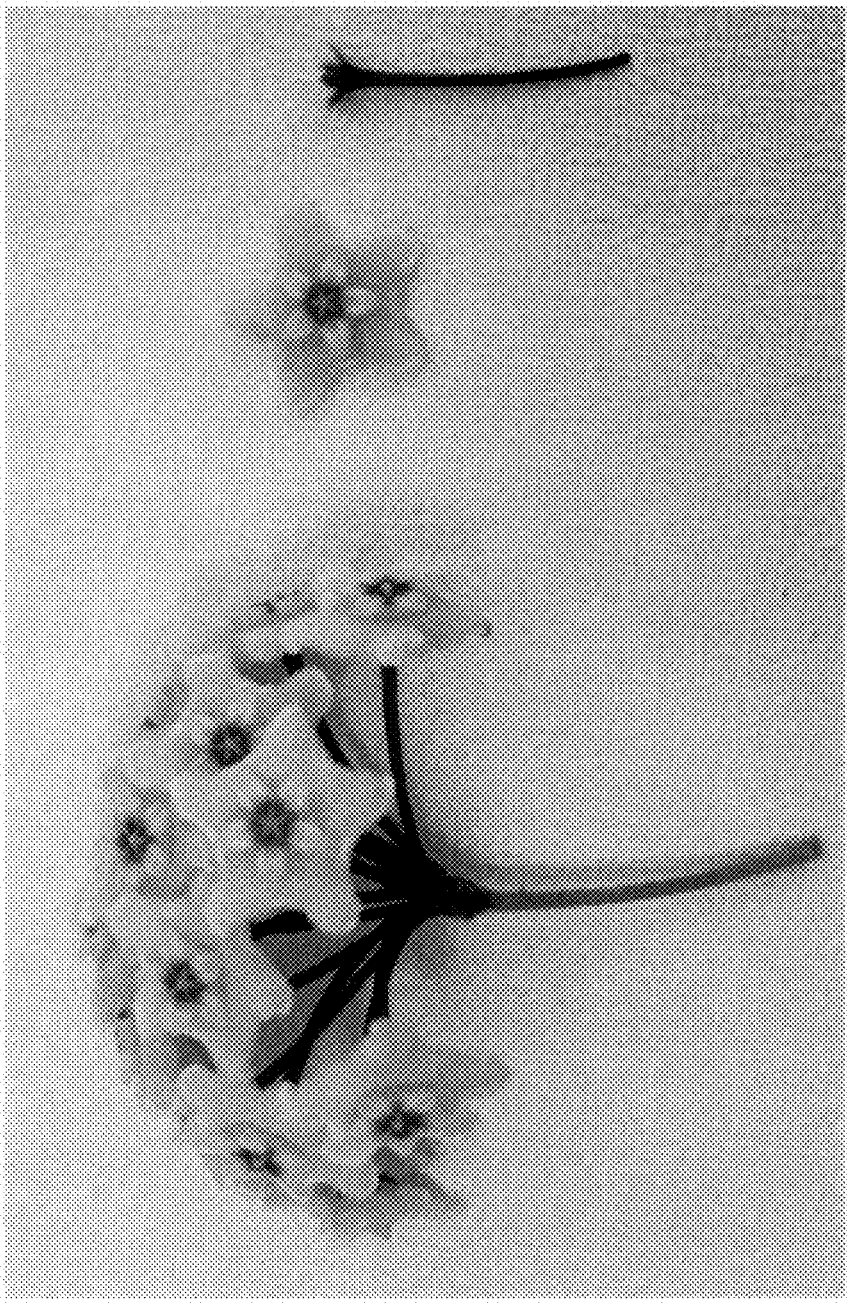
FIG. 2 is a close-up view of the inflorescence.
Figure 3:
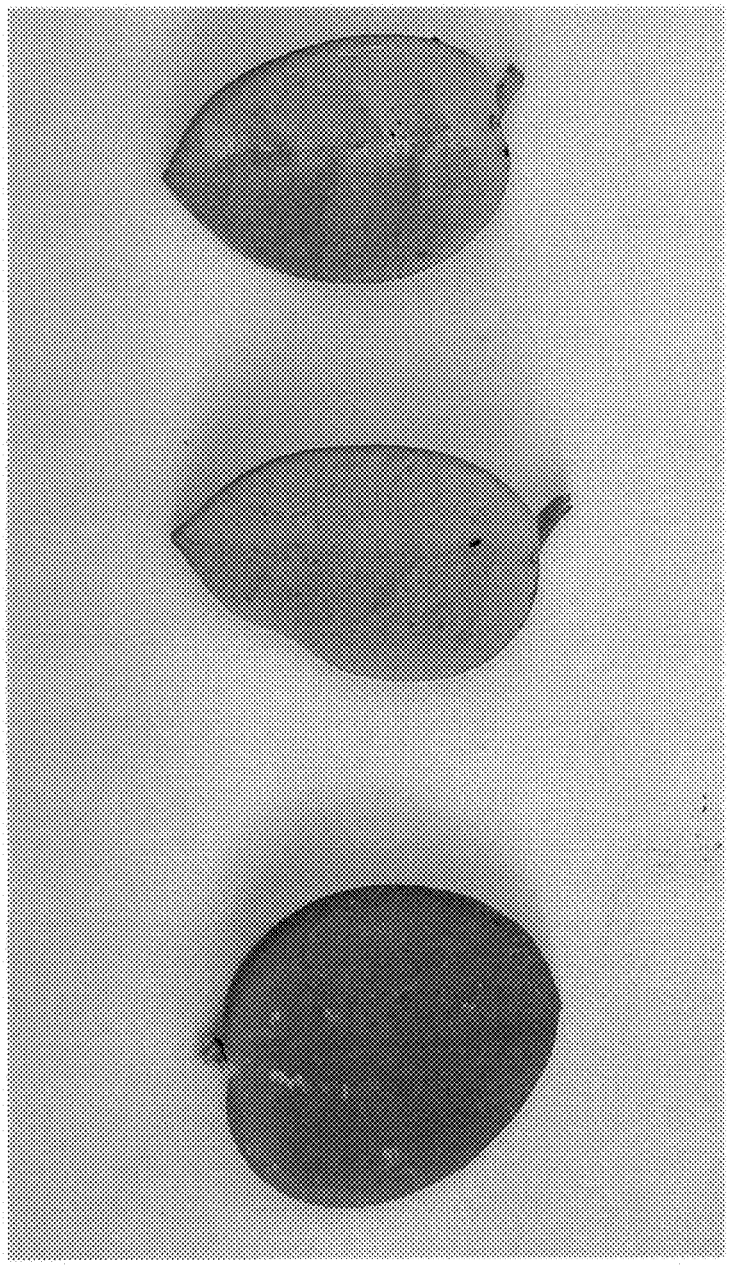
FIG. 3 illustrates 3 typical leaves from a plant of 'GREY FAIRY'. The foliage on the far left is the most mature, center is half-mature and the right immature.
Figure 4:
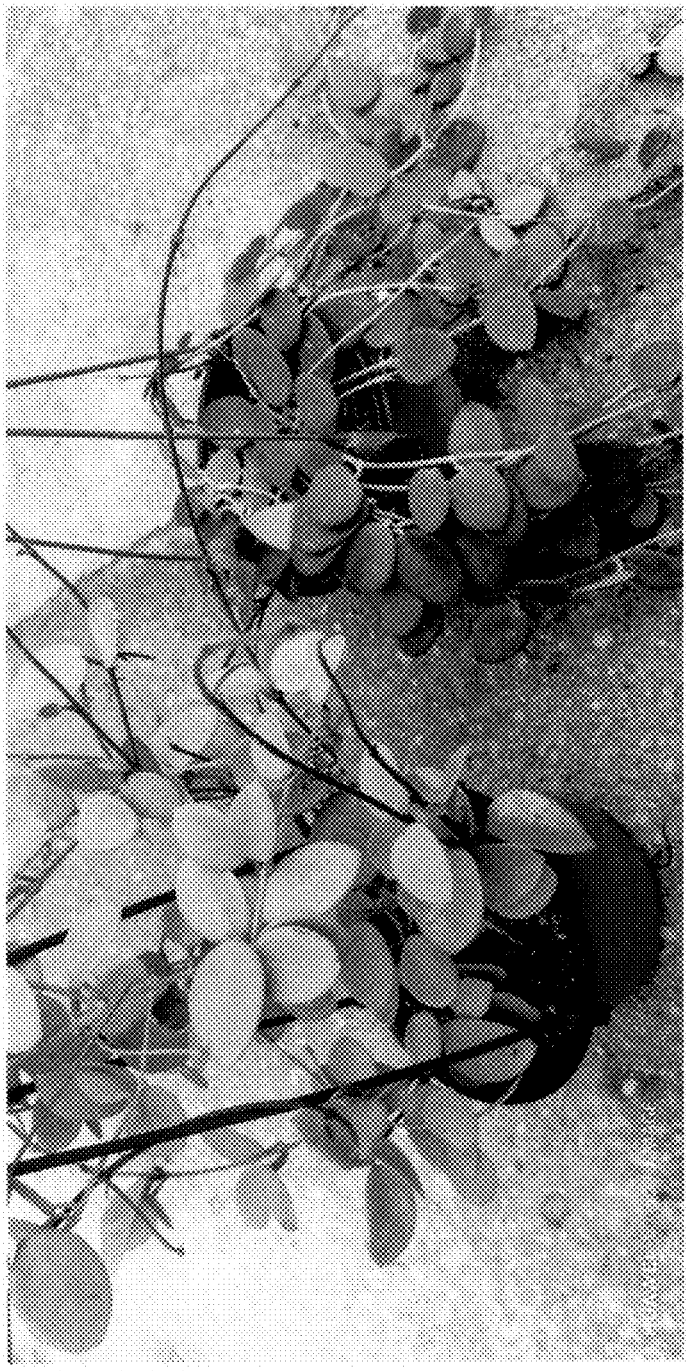
FIG. 4 is a comparison with the parent variety. GREY FAIRY' is on the left, the parent variety is on the right.

Plants were grown in Chuzhou, China in a greenhouse and approximately 2 years old when photographed. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'GREY FAIRY' plants grown in a greenhouse in Chuzhou, China. Temperatures ranged from 16° C. at night to 22° C. during the day. No artificial light, photoperiodic treatments were given to the plants. Measurements and numerical values represent averages of typical plant types.

Botanical classification: *Hoya carnosa* x *serpens* 'Grey Fairy'

Roots

Root structure:
- *Length*.—11.3 cm.
- *Diameter*.—0.1 cm.
- *Texture*.—Fleshy.
- *Color*.—RHS White 155B.
- *Typical root shape in cross section*.—Irregular round.

PROPAGATION

Time to initiate roots: About 10 to 12 days at approximately 30° C. in the summer. About 20 days at 18° C. in the winter.

Time to produce a rooted cutting: About 30 to 40 days at 20° to 30° C.

PLANT

Plant type: Tender perennial flowering vine.
Age of plant described: 2 years.
Container size: 10 to 15 cm.
Height: 58 cm.
Plant spread: 46 cm.
Growth rate: High.
Plant vigor: High.
Branching characteristics: Basal (stems); no pinching required.
Primary branch length: Average range 40 to 55 cm.
Primary branch diameter: 2 mm.
Internode length: 0.8 to 4.4 cm.
Stem:
- *Aspect*.—Spread.
- *Strength*.—Weak.
- *Texture*.—Pubescent.
- *Luster*.—Matte.
- *Color*.—Developing: RHS Reddish-Brown 165A. At internodes: RHS Green 138C. Developed: RHS Green 139A.

FOLIAGE

Leaf:
- *Arrangement*.—Opposite, single.
- *Average length*.—2.7 to 3.8 cm.
- *Average width*.—1.9 to 2.6 cm.
- *Shape of blade*.—Orbicular.
- *Apex*.—Obtuse.
- *Base*.—Obtuse.
- *Margin*.—Entire.
- *Texture*.—Fleshy, both surfaces.
- *Pubescence*.—Both sides.
- *Luster*.—Upper Side: Weak. Under Side: Weak.
- *Color*.—Young Foliage, Upper Side: RHS Green 135A with overlay 133C. Young Foliage, Under Side: RHS Yellow-Green 141B. Mature Foliage, Upper Side: RHS Green N138C. Mature Foliage, Under Side: RHS Green 138B. Autumn Foliage, Upper Side: RHS Green N138C. Autumn Foliage, Under Side: RHS Green 138B.
- *Venation*.—Type: Pinnate. Color Upper Side: RHS Green N138C. Color Under Side: RHS Green 138B.
- *Petiole*.—Length: 1.2 cm. Diameter: 0.2 cm. Color, Upper Side: RHS Green 137A. Color, Under Side: RHS Green 137B. Texture: Fleshy. Luster: Weak. Strength: Weak.

FLOWER

Natural flowering season: Spring and summer.
Flower arrangement: Cymose umbel.
Flower type and form: Hemisphere.
Inflorescence type and form: Umbelliform.
Quantity of flowers: 20 to 30 per inflorescence; 10 to 20 inflorescences per plant.
Quantity of buds: 20 to 30 per inflorescence.
Flower longevity: 4 to 7 days.
Inflorescence size:
- *Diameter*.—5.5 cm.
- *Height*.—5.4 cm.

Bud:
- *Shape*.—Star.
- *Length*.—0.4 cm.
- *Diameter*.—0.9 cm.
- *Color*.—RHS Yellow 13D; Red-Purple 61D in center.
- *Texture*.—Waxy.
- *Luster*.—High.

Flower:
- *Shape*.—Star.
- *Height*.—2.7 cm.
- *Diameter*.—1.6 cm.
- *Length*.—0.4 cm.

Petals:
- *Arrangement*: Double whorl.
- *Quantity:* 10 per flower.
- *Shape*: Ovate.
- *Length*: Corolla 0.7 cm; corona 0.4 cm.
- *Width*: Corolla 0.5 cm; corona 0.2 cm.
- *Margin*: Lightly ciliate.
- *Apex*: Acute.
- *Base*: Fused.
- *Texture, both sides*: Corolla: pubescent; corona: waxy.
- *Rugosity, both sides*: Corolla: pubescent; corona: waxy.
- *Luster, both sides*: Corolla: weak; corona: high.
- *Color*: When opening: Upper surface: Corolla: RHS White N155C; Corona: White 155B, Purple-Red 60B in center. Lower surface: Corolla: RHS White N155C; Corona: White 155B, Purple-Red 60B in center. Fully opened: Upper surface: Corolla: RHS White N155C; Corona: White 155B, Purple-Red 60B in center. Lower surface: Corolla: RHS White N155C; Corona: White 155B, Purple-Red 60B in center. Fading: Upper surface: Corolla: RHS Orange N170A; Corona: White 155D. Lower surface: Corolla: RHS Orange N170A; Corona: White 155D.

Sepals:
- *Arrangement*.—Single whorl.
- *Shape*.—Ovate.
- *Quantity*.—5 per flower.
- *Length*.—0.2 cm.
- *Width*.—0.1 cm.
- *Margin*.—Entire.

*Apex*.—Acute.

*Base*.—Fused.

*Texture, both sides*.—Papery.

*Luster, upper side*.—Medium.

*Luster, under side*.—Weak.

*Color*.—When opening: Upper Surface: RHS Purple-Red 59A. Lower Surface: RHS Purple-Red 59B. Fully opened: Upper Surface: RHS Purple-Red 59A. Lower Surface: RHS Purple-Red 59B.

Calyx:

*Shape*.—Narrow ovate.

*Length*.—0.2 cm.

*Diameter*.—0.5 cm.

Peduncles:

*Length*.—4.5 cm.

*Width*.—0.2 cm.

*Angle*.—15° to 45°.

*Strength*.—Weak.

*Texture*.—Fleshy.

*Luster*: Weak.

*Color*: RHS Brown 165A.

Pedicels:

*Length:* 2.3 cm.

*Diameter:* 0.1 cm.

*Aspect:* 135° to 165°.

*Strength*: Weak.

*Texture*: Fleshy.

*Luster*: Weak.

*Color*: RHS Brown 166A.

Fragrance: Moderate, sweet.

REPRODUCTIVE ORGANS

Androecium

Stamens: Appressed to stigma, no distinguishable parts.

*Pollen amount*: Low.

*Pollen color*: Yellow, near 7B.

Gynoecium

Pistil:

*Number:* 1.

*Length:* 0.1 cm.

*Stigma*: Shape: Oval. Diameter: 0.1 cm. Color: White, too minute to identify with a color chart. Ovary Color: RHS Red 60A on top; Yellow-Green 140B at base.

OTHER CHARACTERISTICS

Disease resistance: High resistance to normal diseases and pests of Hoya have been observed. Typical pests of Hoya include aphid (Aphis nerii), red spider mite (Tetranychus tumidus) and scale (Coccus hesperidum). The most common disease found in Hoya, in the inventor's experience is Anthracnose (Colletotrichum sp.).

Drought tolerance and cold tolerance: Tolerates temperatures from approximately 3° C. to 45° C. Moderate tolerance to rain. High tolerance to wind.

Fruit/seed production: Not observed.

What is claimed is:

1. A new and distinct cultivar of *Hoya* plant named 'GREY FAIRY' as herein illustrated and described.

* * * * *